United States Patent [19]

Minatono et al.

[11] 4,362,841

[45] Dec. 7, 1982

[54] HYDROUS GEL

[75] Inventors: Shobu Minatono; Hideo Takamatsu, both of Ibaraki, Japan

[73] Assignee: Kuraray Co., Ltd., Kurashiki, Japan

[21] Appl. No.: 120,829

[22] Filed: Feb. 12, 1980

[30] Foreign Application Priority Data

Feb. 13, 1979 [JP] Japan .................................. 54/15586

[51] Int. Cl.$^3$ ........................... C08L 9/00; C08L 13/00
[52] U.S. Cl. ..................................... 524/531; 128/156; 252/522 A; 424/78; 424/83; 524/571; 524/801; 524/916
[58] Field of Search ............................... 252/309, 316; 260/29.7 GP, 29.7 M, 29.7 W, 42.32; 524/571, 574, 801, 916, 531

[56] References Cited

U.S. PATENT DOCUMENTS

| | | | |
|---|---|---|---|
| 3,036,980 | 5/1962 | Dunham, Jr. et al. | 260/42.32 X |
| 3,673,142 | 6/1972 | Saunders et al. | 260/29.7 W X |
| 3,799,903 | 3/1974 | Najvar | 260/29.7 M X |
| 3,898,193 | 8/1975 | Minatono et al. | 260/42.32 X |
| 4,102,807 | 7/1978 | Iwama et al. | 252/309 X |
| 4,157,995 | 6/1979 | Schenck et al. | 260/29.7 W X |

*Primary Examiner*—Richard D. Lovering
*Attorney, Agent, or Firm*—Oblon, Fisher, Spivak, McClelland & Maier

[57] ABSTRACT

A hydrous gel consisting essentially of a water-in-oil dispersion cured with a crosslinking agent. The dispersion comprises a rubber component in which water is dispersed in the form of droplets in the presence of a surfactant. The rubber component is based on a liquid polyisoprene rubber having a cis-1,4 content of not less than 70% and a molecular weight of 8,000 to 120,000 or a modified polyisoprene rubber which is an adduct of the above-mentioned liquid polyisoprene rubber and maleic anhydride or a derivative thereof. The hydrous gel provides cold- and heat-retaining materials, perfume-retaining materials, adhesives for medical use, poultices and shock-absorbing materials.

13 Claims, No Drawings

HYDROUS GEL

BACKGROUND OF THE INVENTION

1. Field of the Invention

This invention relates to a hydrous gel essentially consisting of a cured water-in-oil emulsion in which a liquid rubber is used.

2. Description of the Prior Art

Heretofore hydrous gels comprising water soluble polymers such as polyvinyl alcohol, polyacrylic acid, cellulosic polymers and starch have been used as cold- and heat-retaining materials, perfume-retaining materials and shock-absorbing materials and for other various purposes. However, those hydrous gels that are formed following gelation of aqueous solutions of water soluble polymers properly function only in a very limited temperature range, such as in the neighborhood of ordinary temperatures. At temperatures low enough to freeze water, such a hydrous gel is frozen as a whole and turns into a very hard, rigid mass. Conversely, at high temperatures, water evaporates rapidly unless the hydrous gel is held in a tightly closed container, and the remaining mass no longer functions as a hydrous gel; in some cases flow of the material which may occur at places where the points of crosslinking are scarce or the crosslinking bonds are weak may cause various troubles. In using such a hydrous gel, various problems are encountered due to such troubles. Thus, for example, when used as a cold-retaining material, the hydrous gel is frozen as a whole and thereby loses its original flexibility and gives a bad, unpleasant feeling to the human body when it is cooled therewith and moreover it is difficult to cool efficiently those human body parts that rise and fall in a complicated manner. In cases where the hydrous gel is used as a perfume-retaining material, an increase in temperature results in an increased rate of water evaporation, which in turn inevitably causes an accelerated volatilization of the perfume ingredient; and as a result the perfume performance is lost in a very short period of time. Therefore, in the areas of cold- and heat-retaining materials, perfume-retaining materials, shock-absorbing materials and so forth, a hydrous gel which is constant in its function over a wide temperature range is in great demand. A polymeric material satisfying the requirement that the change in its performance characteristics is small over a wide temperature range can be prepared by crosslinking a rubber-like material having a low glass transition point, and it is expected that the above requirement can be met in principle by a cured product from a water-in-oil dispersion in which water is dispersed in the form of droplets in a continuous phase of the above-mentioned rubber-like material.

In fact, some techniques have been proposed in relation to preparing hydrous gels by crosslinking water-in-oil dispersions in which water is dispersed in the form of droplets in rubber components based on natural rubbers, polybutadiene rubbers, other solid rubbers, ethylene-vinyl acetate copolymers, styrene-butadiene copolymers, styrene-isoprene rubber copolymers or other thermoplastic rubbers. However, each technique has its own problems and moreover, the hydrous gel obtained after crosslinking the dispersion does not always have satisfactory performance characteristics. Thus, when a solid rubber such as a natural rubber is used, its viscosity is so high that water practically cannot be emulsufied therein at temperatures below 100° C. even with the use of a small amount of a plasticizer. The technique consisting in dispersing water in a solution of a solid rubber in an organic solvent alone can be considered only as a suggestion; there has been no successful method proposed to remove the organic solvent alone from the hydrous gel so prepared. In the case of the Akio Iwama et al. invention, U.S. Pat. No. 4,102,807, which uses a thermoplastic rubber, a temperature of 150° C. or above is required at the time of emulsification and dispersion of water unless a plasticizer is used. Even when a large amount of a plasticizer is used, it is still necessary to mix the thermoplasic rubber and the plasticizer in advance at such high temperatures as 120° C. to 150° C., so that the processability is far from satisfactory. Moreover, the hydrous gel finally obtained is inferior in heat durability because the points of crosslinking in the thermoplastic rubber involve physical bonds alone. Thus, when the temperature reaches and exceeds 60° C., the crosslinking points clearly show a tendency toward softening. In addition, since the thermoplastic rubber generally contains in part those copolymer portions that have high glass transition temperatures, the rubber component, when kept at low temperatures, partly hardens even if the whole rubber component is not crystallized, and as a result the hydrous gel as a whole becomes rather hard and rigid.

SUMMARY OF THE INVENTION

The present invention removes the above drawbacks of the prior art. A principal object of the invention is to provide a hydrous gel which can properly fulfil its function over a wide temperature range. Another object is to provide a method of preparing such a hydrous gel. A further object is to provide a stable water-in-oil emulsion. A still further object is to provide cold- or heat-retaining materials, perfume-retaining materials, adhesives for medical use, poultices and shock-absorbing materials.

According to the invention, the above objects are achieved by a hydrous gel consisting essentially of a water-in-oil dispersion cured with a crosslinking agent, said dispersion comprising a rubber component in which water is dispersed in the form of droplets in the presence of a surfactant, said rubber component being based on a liquid polyisoprene rubber having a cis-1,4 content of not less than 70% and a molecular weight of 8,000 to 120,000 or a modified liquid polyisoprene rubber which is an adduct of said liquid polyisoprene rubber and maleic anhydride or a derivative thereof.

DETAILED DESCRIPTION OF THE PREFERRED EMBODIMENTS

The rubber component to be used as an essential component according to the invention is based on the liquid polyisoprene rubber as mentioned above or a modified polyisoprene rubber which is an adduct of such liquid polyisoprene rubber and maleic anhydride or a derivative thereof. The liquid polyisoprene rubber is strictly specified in respect of its molecular weight and microstructure. Thus, the molecular weight should be in the range of 8,000 to 120,000. When the molecular weight is much higher than 120,000, it is no longer easy to carry out the emulsification/dispersion procedure, it is no longer possible to obtain stable water-in-oil dispersions, it is no longer easy to obtain crosslinkable products therefrom and, if obtained, the crosslinked products will not be homogeneous. Conversely, when the molecular weight is much lower than 8,000, the emulsification procedure itself becomes easy, but the efficiency of the crosslinking between rubber molecules is greatly decreased when the water-in-oil dispersion is crosslinked and as a result the product gel is too fluid, lacks ability to retain its form and cannot properly function any longer. From these considerations, it is preferred that the molecular weight be in the range of 12,000 to 78,000. The term "molecular weight" used herein means the viscosity-average molecular weight (abbreviated to "Mv") which is calculated from the following equation:

$$[\eta] = 1.21 \times 10^{-4} Mv^{0.77}$$

where $[\eta]$ is the intrinsic viscosity as determined in toluene solution at 30° C.

Moreover, it is necessary that the cis-1,4 content of the unmodified liquid polyisoprene rubber not be less than 70%, preferably not less than 75%. In case the cis-1,4 content is too low, the result is not only decreased emulsifiability and dispersibility, presumably due to rigidity of the liquid polyisoprene rubber molecule chains themselves, but also inferior low temperature performance of the hydrous gel prepared from the resulting water-in-oil dispersion by crosslinking the same.

The unmodified liquid polyisoprene rubber with such specific molecular weight and cis-1,4 content can be prepared, for example, by Ziegler polymerization, anionic polymerization or some other known polymerization techniques. It can also be prepared by thermal decomposition at a high temperature of a high molecular weight isoprene polymer or a natural rubber, although production of thermal decomposition products of a constant quality is often difficult. The most preferred liquid polyisoprene rubbers are those which are produced by anionic polymerization, especially using a lithium catalyst, because they contain relatively low proportions of vinyl groups which cause a decrease in rubber elasticity and they contain high proportions of those carbon-carbon double bonds that produce great effects upon rubber elasticity and vulcanizability as well as those cis-1,4 bondings that cause flexibility, and because the polymerization procedure is relatively simple. So long as the liquid polyisoprene rubber has a molecular weight and a microstructure as respectively specified herein, it may be a copolymer with a small amount of such a comonomer as butadiene.

The anionic polymerization will now be described in more detail. Isoprene monomer is polymerized by the use of metallic lithium or an organolithium such as methyl lithium, propyl lithium, butyl lithium or distyrenyl lithium as a catalyst, in the presence or absence of a solvent. As is well known, the molecular weight of the polymer can easily be regulated by adjusting the ratio of the amount of isoprene monomer to that of the catalyst used. The use of a solvent facilitates the control of the polymerization, and, therefore, is appropriate.

The modified liquid polyisoprene rubber to be used according to the invention includes those adducts of maleic anhydride or derivatives thereof that are obtained by reaction of the liquid rubber mentioned above with maleic anhydride and/or a derivative thereof such as a maleic acid, a maleate ester, maleamide or maleimide, as well as products derived from the adduct of a liquid polyisoprene rubber and maleic anhydride by esterifying, amidating or imidating one or both of the carboxyl groups originating from the maleic anhydride with an alcohol, such as methanol, ethanol or n-propanol, or ammonia or an amine such as n-propylamine or n-butylamine, in the presence or absence of a catalyst, such as p-toluene sulfonic acid, according to circumstances. In consideration of the viscosity stability when the modified liquid polyisoprene rubber is to be stored for a long period of time, alcohol derivatives or amine derivatives of the modified liquid polyisoprene rubber are preferred to the maleic-anhydride-modified liquid polyisoprene rubber itself.

The addition reaction of maleic anhydride or a derivative thereof to the liquid polyisoprene rubber can easily be carried out, for example, by adding maleic anhydride or a derivative thereof to a liquid polyisoprene rubber with a molecular weight falling within the above specified range and heating the mixture in the presence or absence of a solvent and in the presence or absence of a radical initiator. The solvent usable herein is generally a hydrocarbon, a halogenated hydrocarbon or the like, and preferably such an inert solvent as n-heptane, n-hexane, n-butane, cyclohexane, benzene, toluene or xylene.

The level of addition of maleic anhydride or a derivative thereof to the liquid polyisoprene rubber should be not more than 15 mole % per isoprene monomer unit in said liquid polyisoprene rubber. With a higher level of addition, the viscosity of the liquid polyisoprene rubber is too high, the emulsifiability is thereby decreased and, further, it is difficult to obtain water-in-oil dispersons, presumably due to an increase in affinity for water caused by the addition of a large proportion of functional groups. On the other hand, for producing hydrous gels by making use of the functional groups added to the liquid polyisoprene rubber, it is necessary that the level of addition be not less than 0.1 mole %. From these considerations, it is desirable that the level of addition be 0.3 to 7 mole %. Such a modified liquid polyisoprene rubber can be crosslinked via the functional groups added and therefore a greater variety of crosslinking agents can be used, hence the modified rubber is often preferred to the unmodified liquid polyisoprene rubber.

The surfactant to be used in practicing the invention may be any surfactant having an H.L.B. (hydrophilic lipophilic balance) value in the range of 2 to 12, preferably in the range of 4 to 10. Typical examples are polyoxyethylene oleyl ether, polyoxyethylene lauryl ether, polyoxyethylene alkylphenyl ether, polyoxyethylene oleate ester, polyoxypropylene polyoxyethylene ester, sorbitan oleate, sorbitan stearate, sorbitan laurate, glycerol fatty acid ester, polyoxyethylenesorbitan oleate and polyoxyethylenesorbitan laurate. Among these, preferred are polyoxyethylene nonylphenyl ether and polyethylene glycol oleyl ether. These can be used either alone or in combination of two or more.

The crosslinking or curing agent to be used in practicing the invention includes those used in conventional vulcanization processes, such as sulfur, peroxides and quinoids. These are generally used in combination with such vulcanization auxiliaries as accelerators and the crosslinking is carried out in a conventional manner. For the modified liquid polyisoprene rubber, besides those mentioned above, such crosslinking agents can be used as metalic compounds, amines, epoxy compounds, glycols and isocyanates.

Preferred metal compounds used as the crosslinking agents are lead compounds, especially lead oxide, zinc compounds such as zinc oxide, zinc acetate and zinc resinate and calcium compounds such as calcium oxide, calcium hydroxide and calcium resinate. Examples of the amine crosslinking agents are dibutylamine, n-propylamine, tripropanolamine, triethylenetetramine, tetraethylenepentamine, polyethylenimine, polyamide resin and methylolmelamine resin. Preferred are tripropanolamine and tetraethylenepentamine. The epoxy crosslinking agents are, for example, epoxy compounds prepared by condensation of an epihalohydrin and a polyol such as diphenylolpropane (bisphenol A), diphenylolmethane (bisphenol F) and tetrakis(hydroxyphenyl)ethane. Especially preferred are those epoxy compounds that are prepared by condensation of epichlorohydrin and bisphenol A and have epoxy equivalents of about 150 to about 700. Among the above-mentioned crosslinking agents, preferred are sulfur, the metal compounds, the amines and the epoxy compounds. The amount of the crosslinking agent depends on the kind of the agent, the temperature at which crosslinking is effected and other factors. In the case of crosslinking making use of the polar groups of maleic anhydride or a derivative thereof, the amount of the crosslinking agent is 0.5 equivalent or more based on the maleic anhydride or the derivative thereof. On the other hand, in view of the fact that the crosslinking agent also serves as a filler, the amount should be not more than 100 parts by weight per 100 parts by weight of the liquid polyisoprene rubber.

A typical procedure for producing the hydrous gel of the invention is described in the following by way of example.

The rubber component based on the liquid polyisoprene rubber or the modified liquid polyisoprene rubber is mixed with the crosslinking agent and optionally with a plasticizer such as an oil, liquid paraffin or dioctyl phthalate, a filler such as silica, clay or calcium carbonate, an antioxidant, a colorant, a perfume, a tackifier, a medicinal ingredient such as powdered capsicum, 1-menthol or methyl salicylate, etc. If necessary, heat may be used. Considering that water is subsequently emulsified and dispersed in the mixture, the heating is preferably carried out to and at a temperature below the boiling point of water. The use of a large amount of a plasticizer presents problems such as plasticizer migration and therefore is not preferred. When process oil is used as a plasticizer, for instance, generally its amount should preferably be not more than 200 parts by weight per 100 parts by weight of the liquid polyisoprene rubber. However, when plasticizer migration is of little concern and just a hydrous gel having a very soft touch is desired, 500 parts by weight or more of process oil may be used. A surfactant is then added to the rubber mixture so prepared. An appropriate amount of water is added to the resulting mixture with stirring, to prepare a water-in-oil dispersion in which water is dispersed in the form of droplets in a continuous phase of the rubber component. The surfactant may be added to the water prior to dispersing the water. The amount of water is 4 to 400 parts by weight per 100 parts by weight of the rubber component including the liquid polyisoprene rubber or the modified liquid polyisoprene rubber and the crosslinking agent or optionally plasticizer. In view of the function of the hydrous gel and the stability of the water droplets, it is preferable to use 25 to 250 parts by weight of water. The resulting water-in-oil dispersion is either stored as it is in an appropriate container at room temperature or cured and shaped into a hydrous gel by crosslinking at adequate temperatures.

The hydrous gel of the invention made in the manner mentioned above is fitted for use as a cold- or heat-retaining material, a perfume-retaining material, an adhesive for medical use, in preparing a poultice, or as a shock absorbing material such as in a bedsore-free bed.

The following examples illustrate the present invention more specifically. It is to be noted, however, that they do not in any way limit the present invention.

EXAMPLE 1

A liquid polyisoprene rubber having a cis-1,4 content of 79% and a molecular weight of 19,000 was prepared by the anionic polymerization method. In a mixer equipped with an impeller-type stirrer, there were added and mixed well 100 parts by weight of the above liquid polyisoprene rubber, 4 parts by weight of zinc stearate, 3 parts by weight of sulfur, and as vulcanization accelerators, 4 parts by weight of zinc dimethyldithiocarbamate (NOCCELER PZ), 3 parts by weight of 2-mercaptobenzothiazole (NOCCELER M) and 3 parts by weight of zinc butylxanthate (NOCCELER ZBX). (NOCCELER PZ, NOCCELER M and NOCCELER ZBX are trademarks of Ouchi Shinko Kagaku Kogyo K.K.). Then, to this mixture was added 15 parts by weight of polyoxyethylene nonylphenyl ether having an H.L.B. value of 7.8 and the resulting mixture was mixed well. Finally, there was added 100 parts by weight of water with stirring. Thus, was obtained a stable water-in-oil dispersion in a very simple manner.

A hydrous gel was produced by allowing the water-in-oil dispersion to stand in an atmosphere maintained at 45° C. for 24 hours so as to cause crosslinking of the rubber component.

The hydrous gel was allowed to stand in a freezer at −20° C. for 24 hours, then taken out into an atmosphere at room temperature and pressed with a finger. The hydrous gel retained the rubber elasticity and flexibility. A part of the mixture just prior to the addition of water as obtained in the course of the preparation of the above water-in-oil dispersion was cured and shaped in the form of a 3 cm cube block to prepare a rubber vulcanizate. Separately, a cubic specimen of the same size was prepared from the hydrous gel as obtained in this example. Both the cubes were allowed to stand at −20° C. for 8 hours and then taken out into the atmosphere at room temperature. An hour later, the temperature at the center of each cube was measured by means of a thermocouple. The temperature of the rubber vulcanizate free of water was 20° C., which was close to room temperature, while that of the hydrous gel of this example was 0° C., proving the superiority of the hydrous gel in retaining the cold. Furthermore, the hydrous gel of this example was allowed to stand at 70° C. for 7 days, during which no appearance of softening or any dimensional change was observed; excellent heat resistance was thus confirmed.

COMPARATIVE EXAMPLE 1

To 10 parts by weight of a teleblock copolymer elastomer of the polystyrene-polybutadiene-polystyrene type, Cariflex TR (trademark of Shell Chemical Co.), heated at 130° C., there was added 10, 30 or 50 parts by weight of a naphthenic process oil, and then 20, 40 or 60 parts by weight of an aqueous dispersion of polyoxyethylene nonylphenyl ether having an H.L.B. value of 8.9 was added in an attempt to cause emulsification. When the process oil was added respectively in an amount of 10 parts by weight, however, it was difficult to attain emulsification.

The water-in-oil emulsions respectively obtained with 30 and 50 parts by weight of the process oil were cooled to room temperature. The resulting hydrous gels were allowed to stand at 70° C. for 7 days. Even the hydrous gel obtained with 30 parts by weight of the process oil exhibited softening and a remarkable change in shape; it was thus demonstrated that these hydrous gels were inferior in heat durability.

EXAMPLE 2

A liquid polyisoprene rubber having a cis-1,4 content of 83% and a molecular weight of 35,000 was prepared by anionic polymerization. To 100 parts by weight of this liquid polyisoprene rubber, there were added 100 parts by weight of a naphthenic process oil, 5 parts by weight of zinc oxide and, as vulcanization accelerators, 3 parts by weight of zinc dimethyldithiocarbamate (NOCCELER PZ), 5 parts by weight of 2-mercaptobenzothiazole (NOCCELER M) and 5 parts by weight of zinc salt of 2-mercaptobenzothiazole (NOCCELER MZ). After thorough mixing, 10 parts by weight of polyoxyethylene nonylphenyl ether having an H.L.B. value of 5.7 was added as a surfactant. Thereafter, a suspension of 5 parts by weight of polyoxyethylene nonylphenyl ether having an H.L.B. value of 8.9 in 200 parts by weight of water was added gradually with stirring. There was obtained a very stable water-in-oil dispersion.

A polyvinyl chloride bag (50 cm×50 cm, 1 cm in thickness when filled) was filled with the water-in-oil dispersion so prepared, then sealed, and stored in an atmosphere maintained at 60° C. for 24 hours, to effect crosslinking.

The resulting hydrous gel was kept in a freezer at −25° C. for 8 hours and then taken out into a room, and its hardness was measured by means of a C-type hardness tester (Kobunshi Keiki K.K.). The hardness was 28. This hydrous gel was soft and flexible, could be wound round the ankle, and was effective as a wet compress. These advantages could be verified when compared, for example, with a hydrous gel prepared by mixing 100 parts by weight of polyvinyl alcohol POVAL 205 (Kuraray Co., LTD.), 100 parts by weight of water and a curing agent, filling a polyvinyl chloride bag with the mixture and effecting crosslinking, which hydrous gel had a hardness of 98, was very hard and could not be wound round the ankle.

EXAMPLE 3

A modified polyisoprene rubber was prepared by reacting 100 parts by weight of a liquid polyisoprene rubber prepared by anionic polymerization and having a cis-1,4 content of 82% and a molecular weight of 27,000 and 6 parts by weight of maleic anhydride at 180° C. in hexane followed by adding methanol to cause esterification; the level of addition of monomethyl maleate was 3.9 mole %. After mixing 100 parts by weight of this modified liquid polyisoprene rubber, 100 parts by weight of a naphthenic process oil, 10 parts by weight of epoxy resin EPIKOTE 828 (Shell Chemical Co.) and 5 parts by weight of tris(dimethylaminomethyl)phenol (Anchor Chemical's K-54) as a cure accelerator, there was added 15 parts by weight of polyoxyethylene oleyl ether having an H.L.B. value of 8.0 as a surfactant. Thereafter, 50 parts of water was added gradually with stirring, to prepare a water-in-oil dispersion. This dispersion was very stable.

This water-in-oil dispersion was poured into a 4 cm cube plastic container and allowed to stand at room temperature for 5 days. The resulting hydrous gel was taken out of the plastic container, allowed to stand in an atmosphere maintained at −20° C. for 24 hours, then taken out into an atmosphere at room temperature and immediately pressed with a finger; the hydrous gel was soft and flexible and well retained the rubber elasticity. Maintaining the hydrous gel at 80° C. for 8 hours did not reveal any tendency to softening and thus its superior heat resistance was proved. In another test, the hydrous gel was allowed to stand at room temperature and the rate of water evaporation was measured. The rate was slow, namely 2% by weight per 10 days, so that the hydrous gel was suited for use as a perfume-retaining material.

COMPARATIVE EXAMPLE 2

A liquid polyisoprene rubber having a cis-1,4 content of 39% and a molecular weight of 21,000 was prepared by anionic polymerization in the presence of an ether compound. Using this liquid polyisoprene rubber whose cis-1,4 content was low and following the procedure of Example 2, a water-in-oil dispersion was prepared. This dispersion was cured by crosslinking as in Example 2, to prepare a hydrous gel. The hydrous gel was allowed to stand at −25° C. for 8 hours, then taken out into the atmosphere at room temperature and immediately subjected to a hardness measurement. It had a hardness of 78 and was hard and rigid.

EXAMPLE 4

To 100 parts by weight of the same liquid polyisoprene rubber as was used in Example 2, there were added 240 parts by weight of a 70/30 mixture of a naphthenic process oil and a polyterpene tackifier, 10 parts by weight of zinc stearate, 4 parts by weight of sulfur, and as vulcanization accelerators, 5 parts by weight of zinc dimethyldithiocarbamate (NOCCELER PZ), 2.5 parts by weight of zinc salt of 2-mercaptobenzothiazole (NOCCELER M) and 7 parts by weight of zinc ethylphenyldithiocarbamate (NOCCELER PX) as well as 1 part by weight of a phenolic antioxidant. After thorough mixing, 30 parts by weight of a surfactant, i.e., polyethylene glycol nonylphenyl ether having an H.L.B. value of 6, was added. To the resulting mixture, 350 parts by weight of water was added gradually with stirring in an atmosphere maintained at 40° C. Thereafter, medicinal ingredients for an adhesive plaster, i.e., 7 parts by weight of methyl salicylate, 4 parts by weight of 1-menthol and 2 parts by weight of camphor, as well as 25 parts by weight of a thickening agent (ultrafine silica) were added. After stirring, there was obtained a stable water-in-oil dispersion.

The water-in-oil dispersion so prepared was applied to a lint cloth to a thickness of 3 mm and a release paper was applied thereon. The laminate was put into a polyethylene bag, the bag was sealed and the whole was allowed to stand in an atmosphere maintained at 45° C. for 24 hours, to cause crosslinking.

The medicated adhesive plaster was agreeable to the skin, allowed the medicinal ingredients to act in an adequate manner, was effective also as a wet compress, and therefore was an excellent product.

Having now fully described the invention, it will be apparent to one of ordinary skill in the art that many changes and modifications can be made thereto without departing from the spirit or scope of the invention as set forth herein.

We claim:

1. A hydrous gel consisting essentially of a water-in-oil dispersion cured with a crosslinking agent, said dispersion comprising a rubber component in which water is dispersed in the form of droplets in the presence of a surfactant, said rubber component being selected from the group consisting of liquid polyisoprene rubber having a cis-1,4 content of not less than 70% and a molecular weight of 8,000 to 120,000, and modified liquid polyisoprene rubber which is an adduct of said liquid polyisoprene rubber and maleic anhydride or a derivative thereof.

2. The hydrous gel of claim 1, wherein the proportion of maleic anhydride or derivative thereof in the modified liquid polyisoprene rubber is 0.1 to 15 mole % based on the isoprene monomer unit.

3. The hydrous gel of claim 1, wherein the rubber component is oil-extended with a process oil in an amount of up to 500 parts by weight per 100 parts by weight of the liquid polyisoprene rubber or the modified liquid polyisoprene rubber.

4. The hydrous gel of claim 1, wherein the water-to-rubber component ratio in the water-in-oil dispersion is 4 to 400 parts by weight of water per 100 parts by weight of the rubber component.

5. The hydrous gel of claim 1, wherein the surfactant is a compound having an H.L.B. (hydrophilic lipophilic balance) value of 2 to 12 and selected from the group consisting of polyoxyethylene oleyl ether, polyoxyethylene lauryl ether, polyoxyethylene alkylphenyl ether, polyoxyethylene oleate ester, polyoxypropylene polyoxyethylene ether, sorbitan oleate, sorbitan stearate, sorbitan laurate, glycerol fatty acid ester, polyoxyethylene-sorbitan oleate and polyoxyethylenesorbitan laurate.

6. The hydrous gel of claim 5, wherein said surfactant is selected from the group consisting of polyoxyethylene nonylphenyl ether and polyethylene glycol oleyl ether.

7. The hydrous gel of claim 1, wherein the crosslinking agent is selected from the group consisting of sulfur, peroxides, metal compound crosslinking agents, amine crosslinking agents, epoxy crosslinking agents, glycol crosslinking agents and isocyanate crosslinking agents.

8. The hydrous gel of claim 1, wherein the crosslinking agent is a metal compound selected from the group consisting of lead oxide, zinc oxide, zinc acetate, zinc resinate, calcium oxide, calcium hydroxide and calcium resinate.

9. The hydrous gel of claim 1, wherein the crosslinking agent is an amine compound selected from the group consisting of dibutylamine, n-propylamine, tripropanolamine, triethylenetetramine, tetraethylenepentamine, polyethyleneimine, polyamide and methylolmelamine resin.

10. The hydrous gel of claim 1, wherein the crosslinking agent is an epoxy compound which is a product of condensation of an ephilaohydrin and a polyol selected from the group consisting of diphenylolpropane, diphenylolmethane and tetrakis(hydroxyphenyl) ethane.

11. The hydrous gel of claim 1, wherein the rubber component is a modified liquid polyisoprene rubber which is an adduct of the liquid polyisoprene rubber and maleic anhydride or a derivative thereof and the crosslinking agent is selected from the group consisting of metal compound, amine, epoxy, glycol and isocyanate crosslinking agents.

12. A hydrous gel prepared by crosslinking a water-in-oil dispersion, said water-in-oil dispersion prepared by mixing a rubber component based on a liquid polyisoprene rubber or modified liquid polyisoprene rubber, a surfactant and a crosslinking agent, adding water and effectng emulsification, said rubber component being selected from the group consisting of liquid polyisoprene rubber having a cis-1,4 content of not less than 70% and a molecular weight of 8,000 to 120,000 and modified liquid polyisoprene rubber which is an adduct of said liquid polyisoprene rubber and maleic anhydride or a derivative thereof.

13. A hydrous gel prepared by crosslinking a water-in-oil dispersion prepared by mixing a rubber component based on a liquid polyisoprene rubber or modified liquid polyisoprene rubber and a cross-linking agent, adding the resulting mixture to an aqueous phase containing a surfactant and effecting emulsification, said rubber component being selected from the group consisting of liquid polyisoprene rubber having a cis-1,4 content of not less than 70% and a molecular weight of 8,000 to 120,000 and modified liquid polyisoprene rubber which is an adduct of said liquid polyisoprene rubber and maleic anhydride or a derivative thereof.

* * * * *